US007968107B2

(12) United States Patent
Baur et al.

(10) Patent No.: US 7,968,107 B2
(45) Date of Patent: Jun. 28, 2011

(54) OIL-BASED SUSPENSION CONCENTRATES

(75) Inventors: Peter Baur, Schondorf (DE); Reiner Fischer, Monheim (DE); Ronald Vermeer, Leverkusen (DE)

(73) Assignee: Bayer Cropscience AG, Monheim (DE)

( * ) Notice: Subject to any disclaimer, the term of this patent is extended or adjusted under 35 U.S.C. 154(b) by 1001 days.

(21) Appl. No.: 10/591,129

(22) PCT Filed: Mar. 4, 2005

(86) PCT No.: PCT/EP2005/002285
§ 371 (c)(1),
(2), (4) Date: Jul. 16, 2007

(87) PCT Pub. No.: WO2005/084435
PCT Pub. Date: Sep. 15, 2005

(65) Prior Publication Data
US 2007/0281860 A1 Dec. 6, 2007

(30) Foreign Application Priority Data
Mar. 6, 2004 (DE) .......................... 10 2004 011 007

(51) Int. Cl.
*A01N 25/00* (2006.01)
*A01N 43/48* (2006.01)
*A01N 43/36* (2006.01)
(52) U.S. Cl. ......... 424/405; 514/341; 514/409; 514/772
(58) Field of Classification Search .................. None
See application file for complete search history.

(56) References Cited

U.S. PATENT DOCUMENTS

| 4,599,412 | A | | 7/1986 | Sandell |
|---|---|---|---|---|
| 4,623,727 | A | | 11/1986 | Hübele |
| 4,639,266 | A | | 1/1987 | Heubach et al. |
| 4,671,817 | A | | 6/1987 | Wexler |
| 4,683,000 | A | | 7/1987 | Petersen |
| 4,881,966 | A | | 11/1989 | Nyffeler et al. |
| 4,891,057 | A | | 1/1990 | Sohn et al. |
| 4,902,340 | A | | 2/1990 | Hübele |
| 5,013,659 | A | | 5/1991 | Bedbrook et al. |
| 5,314,863 | A | | 5/1994 | Löher et al. |
| 5,380,852 | A | | 1/1995 | Schütze et al. |
| 5,401,700 | A | | 3/1995 | Sohn et al. |
| 5,476,936 | A | | 12/1995 | Phillip et al. |
| 5,516,750 | A | | 5/1996 | Willms et al. |
| 5,518,991 | A | | 5/1996 | Frisch et al. |
| 5,573,998 | A | | 11/1996 | Frisch et al. |
| 5,607,898 | A | | 3/1997 | Nakamura et al. |
| 5,700,758 | A | | 12/1997 | Rösch et al. |
| 5,846,907 | A | | 12/1998 | von Deyn et al. |
| 5,925,182 | A | * | 7/1999 | Patel et al. .................... 106/266 |
| 5,990,047 | A | | 11/1999 | Hacker et al. |
| 6,077,813 | A | | 6/2000 | Linker et al. |
| 6,376,429 | B1 | | 4/2002 | Van Almsick et al. |
| 6,420,317 | B1 | | 7/2002 | Schmitt et al. |
| 6,479,432 | B1 | * | 11/2002 | Sixl ............... 504/103 |
| 6,482,947 | B1 | | 11/2002 | Holdgrün et al. |
| 6,559,098 | B1 | | 5/2003 | Bratz et al. |
| 6,569,805 | B1 | | 5/2003 | Krähmer et al. |
| 2002/0016262 | A1 | | 2/2002 | Nakamura et al. |
| 2004/0157745 | A1 | * | 8/2004 | Vermeer et al. ............... 504/362 |
| 2005/0026786 | A1 | | 2/2005 | Deckwer et al. |
| 2005/0214336 | A1 | * | 9/2005 | Turberg et al. ................ 424/405 |
| 2006/0205596 | A1 | | 9/2006 | Deckwer et al. |
| 2006/0276234 | A1 | | 12/2006 | Sixl et al. |
| 2007/0066489 | A1 | | 3/2007 | Vermeer et al. |
| 2007/0129252 | A1 | | 6/2007 | Fischer et al. |
| 2007/0225167 | A1 | | 9/2007 | Fischer et al. |
| 2007/0225170 | A1 | | 9/2007 | Fischer et al. |
| 2007/0265266 | A1 | | 11/2007 | Fischer et al. |
| 2007/0270416 | A1 | | 11/2007 | Funke et al. |
| 2007/0276023 | A1 | | 11/2007 | Fischer et al. |
| 2007/0298969 | A1 | | 12/2007 | Fischer et al. |
| 2008/0027114 | A1 | | 1/2008 | Funke et al. |

FOREIGN PATENT DOCUMENTS

| AU | 666644 B | 2/1996 |
|---|---|---|
| CA | 1 247 880 A | 1/1989 |
| CA | 1340602 C | 6/1999 |
| EP | 0 094 349 A2 | 11/1983 |
| EP | 0 142 924 A2 | 5/1985 |
| EP | 0 163 598 A1 | 12/1985 |
| EP | 0 174 562 A2 | 3/1986 |
| EP | 0 191 736 A2 | 8/1986 |
| EP | 0 193 259 A1 | 9/1986 |
| EP | 0 221 044 A1 | 5/1987 |
| EP | 0 086 750 B1 | 7/1987 |
| EP | 0 245 058 A2 | 11/1987 |
| EP | 0 257 993 A2 | 3/1988 |
| EP | 0 269 806 A1 | 6/1988 |
| EP | 0 303 153 A2 | 2/1989 |
| EP | 0 313 317 A2 | 4/1989 |

(Continued)

OTHER PUBLICATIONS

*AG Chem New Compound Review* 17:24 and 26, Agranova (1999).
Braun, H-P., et al., "The general mitochondrial processing peptidase from potato is an integral part of cytochrome *c* reductase of the respiratory chain," *EMBO J.* 11:3219-3227, Oxford University Press (1992).
Christou, P., "Transformation technology," *Trends Plant Sci.* 1:423-431, Elsevier Science Ltd. (1996).
Falbe, J. and Regitz, M., *Römpp Chemie Lexikon 9*:1343-1345, Georg Thieme Verlag.

(Continued)

*Primary Examiner* — Ernst V Arnold
(74) *Attorney, Agent, or Firm* — Sterne, Kessler, Goldstein & Fox P.L.L.C.

(57) ABSTRACT

New, oil-based suspension concentrates composed of
  at least one room-temperature-solid active agrochemical substance,
  at least one "closed" penetrant,
  at least one vegetable oil or mineral oil,
  at least one nonionic surfactant and/or at least one anionic surfactant, and
  optionally one or more additives from the groups of the emulsifiers, foam inhibitors, preservatives, antioxidants, colorants and/or inert filler materials,
a process for producing these suspension concentrates and their use for applying the active substances comprised.

11 Claims, No Drawings

FOREIGN PATENT DOCUMENTS

| | | |
|---|---|---|
| EP | 0 333 131 A1 | 9/1989 |
| EP | 0 346 620 A1 | 12/1989 |
| EP | 0 492 366 A2 | 7/1992 |
| EP | 0 131 624 B1 | 9/1992 |
| EP | 0 514 768 A1 | 11/1992 |
| EP | 0 514 769 A1 | 11/1992 |
| EP | 0 582 198 B1 | 2/1994 |
| EP | 0 645 386 A1 | 3/1995 |
| EP | 0 764 404 A1 | 3/1997 |
| EP | 0 789 999 A2 | 8/1997 |
| EP | 1 277 405 A1 | 1/2003 |
| WO | WO 91/07874 A1 | 6/1991 |
| WO | WO 91/08202 A1 | 6/1991 |
| WO | WO 91/13972 A1 | 9/1991 |
| WO | WO 91/19806 A1 | 12/1991 |
| WO | WO 92/11376 A1 | 7/1992 |
| WO | WO 92/13845 A1 | 8/1992 |
| WO | WO 92/14827 A1 | 9/1992 |
| WO | WO 93/13658 A1 | 7/1993 |
| WO | WO 95/07897 A1 | 3/1995 |
| WO | WO 95/30661 A1 | 11/1995 |
| WO | WO 96/25412 A1 | 8/1996 |
| WO | WO 96/26206 A1 | 8/1996 |
| WO | WO 96/41537 A1 | 12/1996 |
| WO | WO 97/20467 A1 | 6/1997 |
| WO | WO 97/36868 A1 | 10/1997 |
| WO | WO 98/05638 A2 | 2/1998 |
| WO | WO 98/05638 A3 | 2/1998 |
| WO | WO 98/34482 A1 | 8/1998 |
| WO | WO 00/21924 A1 | 4/2000 |
| WO | WO 00/25586 A1 | 5/2000 |
| WO | WO 01/30155 A2 | 5/2001 |
| WO | WO 01/30155 A3 | 5/2001 |
| WO | WO 01/30156 A1 | 5/2001 |
| WO | WO 01/74785 A1 | 10/2001 |
| WO | WO 01/82693 A2 | 11/2001 |
| WO | WO 01/82693 A3 | 11/2001 |
| WO | WO 03/000053 A1 | 1/2003 |
| WO | WO 03/015519 A1 | 2/2003 |
| WO | WO 03/024222 A1 | 3/2003 |
| WO | WO 03/086075 * | 10/2003 |
| WO | WO 03/099005 A1 | 12/2003 |
| WO | WO 2005/011378 A1 | 2/2005 |
| WO | WO 2005/011382 A1 | 2/2005 |
| WO | WO 2007/042152 A1 | 4/2007 |

OTHER PUBLICATIONS

Marshall, E.J.P., Glossary of Common Names and Abbreviations of Herbicides, *Weed Research* 26:441-445, Blackwell Scientific Publications (1986).

Schlotter, P., et al., "Florasulam—A new herbicide for broadleaf weed control in cereals," *Z. PflKrankh. PflSchutz, Sonderh. XVI*:527-534, Verlag Eugen Ulmer, Stuttgart (1998).

Sonnewald, U., et al., "Trangenic tobacco plants expressing yeast-derived invertase in either the cytosol, vacuole or apoplast: a powerful tool for studying sucrose metabolism and sink/source interactions," *Plant J. 1*:95-106, Blackwell Scientific Publishers (1991).

Wolter, F.P., et al., "*rbcs* genes in *Solanum tuberosum*: Conservation of transit peptide and exon shuffling during evolution," *Proc. Natl. Acad. Sci. USA 85*:846-850, National Academy of Sciences (1988).

Dialog File 351, Accession No. 4963457, Derwent WPI English language abstract for EP 0 346 620 A1, (listed on accompanying PTO/SB/08A as document FP16).

Dialog File 351, Accession No. 8294412, Derwent WPI English language abstract for EP 0 789 999 A2 (listed on accompanying PTO/SB/08A as document FP39).

International Search Report for International Application No. PCT/EP2005/002285, European Patent Office, Netherlands, mailed on Sep. 16, 2005.

International Search Report for International Application No. PCT/EP2005/008839, European Patent Office, Netherlands, mailed on Mar. 17, 2006.

International Search Report for International Application No. PCT/EP2006/009433, European Patent Office, Netherlands, mailed on Jan. 16, 2007.

International Search Report for International Application No. PCT/EP2005/002294, European Patent Office, Netherlands, mailed on Sep. 16, 2005.

Co-pending U.S. Appl. No. 11/632,501, inventors Fischer, R., et al., filed Jul. 18, 2005; not published (Not Published).

Co-pending U.S. Appl. No. 11/666,870, inventors Fischer, R., et al., filed Oct. 21, 2005 (Not Published).

Co-pending U.S. Appl. No. 11/666,988, inventors Fischer, R., et al., filed Oct. 21, 2005; not published (Not Published).

Co-pending U.S. Appl. No. 11/795,714, inventors Fischer, R., et al., Jan. 17, 2006 (Not Published).

Co-pending U.S. Appl. No. 11/884,845, inventors Fischer, R., et al., Feb. 14, 2006 (Not Published).

Co-pending U.S. Appl. No. 12/089,845 inventors Vermeer, R., et al., Sep. 28, 2006 (Not Published).

Falbe, J. and Regitz, M., *Römpp Chemie Lexikon 9*:1343-1345, Georg Thieme Verlag, Stuttgart, N.Y. (1990).

Dialog File 351, Accession No. 4963457, Derwent WPI English language abstract for EP 0 346 620 A1, (listed previously on form PTO/SB/08A as document FP16) (1989).

Dialog File 351, Accession No. 8294412, Derwent WPI English language abstract for EP 0 789 999 A2 (listed previously on form PTO/SB/08A as document FP39) (1997).

* cited by examiner

OIL-BASED SUSPENSION CONCENTRATES

The present invention relates to new, oil-based suspension concentrates of active agrochemical substances, to a process for producing these formulations and to their use for applying the active substances comprised.

Numerous water-free suspension concentrates of active agrochemical substances have already been disclosed. For instance EP-A 0 789 999 describes formulations of this type which in addition to active substance and oil comprise a mixture of different surfactants—including some which serve as penetrants—and also a hydrophobicized aluminophyllosilicate thickener. The stability of these preparations is good. A disadvantage, however, is the mandatory presence of a thickener, since it makes production more complex. Moreover, the thickener absorbs in each case some of the added amount of penetrant; which is therefore unavailable for its proper function.

From U.S. Pat. No. 6,165,940, moreover, non-aqueous suspension concentrates are already known in which besides active agrochemical substance, penetrant and surfactant or surfactant mixture there is an organic solvent, suitable solvents of this type including liquid paraffin or vegetable oil esters. The biological activity and/or crop tolerance and/or the stability of the spray liquors preparable from these formulations by dilution with water is, however, not always sufficient.

DE-A 10 129 855 describes further oil-based suspension concentrates comprising active agrochemical substances, penetrants and surfactants.

The penetrants described in the abovementioned patent applications are "open" alkanol alkoxylates.

New oil-based suspension concentrates have now been found which are composed of
- at least one room-temperature-solid active agrochemical substance,
- at least one "closed" penetrant,
- at least one vegetable oil or mineral oil,
- at least one nonionic surfactant and/or at least one anionic surfactant, and
- optionally one or more additives from the groups of the emulsifiers, foam inhibitors, preservatives, antioxidants, colorants and/or inert filler materials.

Additionally it has been found that the oil-based suspension concentrates of the invention can be produced by mixing
- at least one room-temperature-solid active agrochemical substance,
- at least one "closed" penetrant,
- at least one vegetable oil or mineral oil,
- at least one nonionic surfactant and/or at least one anionic surfactant, and
- optionally one or more additives from the groups of the emulsifiers, foam inhibitors, preservatives, antioxidants, colorants and/or inert filler materials with one another and optionally subsequently grinding the resultant suspension.

Finally it has been found that the oil-based suspension concentrates of the invention are highly suitable for applying the active agrochemical substances comprised to plants and/or their habitat.

It is to be considered extremely surprising that the oil-based suspension concentrates of the invention exhibit a very good stability despite containing no thickener. Also unexpected is the fact that they display a better biological activity and/or crop tolerance than the existing formulations most similar in composition. Surprisingly, moreover, in terms of their activity, the oil-based suspension concentrates of the invention also surpass similar preparations which besides the other components contain either only penetrant or only vegetable oil. No such synergistic effect was foreseeable from the above-described prior art.

Furthermore, it is very surprising that the "closed" penetrants display a better biological activity than the corresponding "open" penetrants.

The oil-based suspension concentrates of the invention are also notable for a series of advantages. For instance, their production is less complex than the preparation of corresponding formulations in which thickeners are present. A further advantage is that, when the concentrates of the invention are diluted with water, there is neither significant creaming nor disruptive flocculation, which is frequently the case with existing preparations of this kind. Finally, the formulations of the invention promote the biological activity of the active components comprised, so that in comparison to conventional preparations either a higher activity is obtained or less active substance is needed.

Solid, active agrochemical substances in the present context are all substances which are usual in the treatment of plants and whose melting point is above 20° C. Mention may be made preferredly of fungicides, bactericides, insecticides, acaricides, nematicides, molluscicides, herbicides, plant growth regulators, plant nutrients, and repellants.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin-5-cyclopentyl-isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone; coumaphos, cyanofenphos, cyanophos, cycloprene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-S-methyl, demeton-S-methylsulphon, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, *Tricoderma atroviride*, triflumuron, trimethacarb, vamidothion, vaniliprole, verbutin, *Verticillium lecanii*, WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3.2.1]-octane-3-carbonitrile (CAS Reg. No. 185982-80-3) and the corresponding 3-endogenous isomer (CAS Reg. No. 185984-60-5) (cf. WO 96/37494, WO 98/25923), and preparations which comprise insecticidally active plant extracts, nematodes, fungi or viruses.

Examples that may be mentioned of plant nutrients include customary inorganic or organic fertilizers for supplying plants with macronutrients and/or micronutrients.

Further examples that may be mentioned of insecticides and acaricides include the following:

Anthranilamides (WO 01/70 671, WO 03/015 518, WO 03/015 519, WO 03/016 284, WO 03/016 282, WO 03/016 283, WO 03/024 222, WO 03/062 226, WO 04/027042 and WO 04/067528), Phthalamides (cf. EP-A-0 919 542, EP-A-1 006 107, WO 01/00575, WO 01/00599, WO 01/46124, JP-A-2001-335559, WO 01/02354, WO 01/21576, WO 02/088074, WO 02/088075, WO 02/094765, WO 02/094766, WO 02/062807) and compounds of the formula (I')

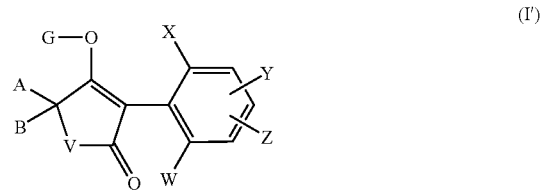

(I')

in which

V is oxygen or N-D,

X is halogen, alkyl, alkoxy, haloalkyl, haloalkoxy or cyano,

W, Y and Z independently of one another are hydrogen, halogen, alkyl, alkoxy, haloalkyl, haloalkoxy or cyano, A is hydrogen, in each case optionally halogen-substituted alkyl, alkoxyalkyl, saturated, optionally substituted cycloalkyl, in which optionally at least one ring atom is replaced by a heteroatom, B is hydrogen or alkyl, A and B together with the carbon atom to which they are attached are a saturated or unsaturated, unsubstituted or substituted ring optionally including at least one heteroatom, D is hydrogen or an optionally substituted radical from the series alkyl, alkenyl, alkoxyalkyl, saturated cycloalkyl, in which optionally one or more ring members are replaced by heteroatoms, A and D together with the atoms to which they are attached are a saturated or unsaturated ring which optionally includes at least one heteroatom and is unsubstituted or substituted in the A, D moiety, G is hydrogen (a) or is one of the groups

(b)

(c)

(d)

-continued

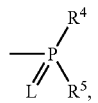
(e)

E or
(f)

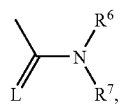
(g)

in which
E is a metal ion or an ammonium ion,
L is oxygen or sulphur,
M is oxygen or sulphur,
$R^1$ is in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, or in each case optionally substituted phenyl, phenylalkyl, hetaryl, phenoxyalkyl or hetaryloxyalkyl,
$R^2$ is in each case optionally halogen-substituted alkyl, alkenyl, alkoxyalkyl, polyalkoxyalkyl or is in each case optionally substituted cycloalkyl, phenyl or benzyl,
$R^3$ is optionally halogen-substituted alkyl or optionally substituted phenyl,
$R^4$ and $R^5$ independently of one another are in each case optionally halogen-substituted alkyl, alkoxy, alkylamino, dialkylamino, alkylthio, alkenylthio, cycloalkylthio or are in each case optionally substituted phenyl, benzyl, phenoxy or phenylthio, and
$R^6$ and $R^7$ independently of one another are hydrogen, in each case optionally halogen-substituted alkyl, cycloalkyl, alkenyl, alkoxy, alkoxyalkyl, are optionally substituted phenyl, are optionally substituted benzyl or together with the nitrogen atom to which they are attached are an optionally oxygen- or sulphur-interrupted optionally substituted ring.

Preference is given to oil-based oil suspension concentrates comprising compounds of the formula (I') in which the radicals have the following definition:
V is preferably oxygen or N-D,
W is preferably hydrogen, $C_1$-$C_4$-alkyl; $C_1$-$C_4$-alkoxy, chlorine, bromine or fluorine,
X is preferably $C_1$-$C_4$-alkyl, $C_1$-$C_4$-alkoxy, $C_1$-$C_4$-haloalkyl, fluorine, chlorine or bromine,
Y and Z are independently of one another preferably hydrogen, $C_1$-$C_4$-alkyl, halogen, $C_1$-$C_4$-alkoxy or $C_1$-$C_4$-haloalkyl,
A is preferably hydrogen or in each case optionally halogen-substituted $C_1$-$C_6$-alkyl or $C_3$-$C_8$-cycloalkyl,
B is preferably hydrogen, methyl or ethyl,
A, B and the carbon atom to which they are attached are preferably saturated $C_3$-$C_6$-cycloalkyl, in which optionally a ring member is replaced by oxygen or sulphur, and which is optionally mono- or disubstituted by $C_1$-$C_4$-alkyl, trifluoromethyl or $C_1$-$C_4$-alkoxy,
D is preferably hydrogen, in each case optionally fluorine- or chlorine-substituted $C_1$-$C_6$-alkyl, $C_3$-$C_4$-alkenyl or $C_3$-$C_6$-cycloalkyl,
A and D are together preferably in each case optionally methyl-substituted $C_3$-$C_4$-alkanediyl, in which optionally a methylene group is replaced by sulphur, G is preferably hydrogen (a) or is one of the groups

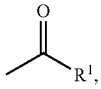
(b)

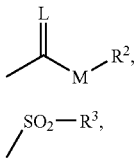
(c)

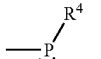
(d)

(e)

E or
(f)

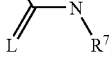
(g)

particularly (a), (b), (c) or (g),
in which
E is a metal ion or an ammonium ion,
L is oxygen or sulphur and
M is oxygen or sulphur,
$R^1$ is preferably in each case optionally halogen-substituted $C_1$-$C_{10}$-alkyl, $C_2$-$C_{10}$-alkenyl, $C_1$-$C_4$-alkoxy-$C_1$-$C_4$-alkyl, $C_1$-$C_4$-alkylthio-$C_1$-$C_4$-alkyl or optionally fluorine-, chlorine-, $C_1$-$C_4$-alkyl- or $C_1$-$C_2$-alkoxy-substituted $C_3$-$C_6$-cycloalkyl,
is optionally fluorine-, chlorine-, bromine-, cyano-, nitro-, $C_1$-$C_4$-alkyl-, $C_1$-$C_4$-alkoxy-, trifluoromethyl- or trifluoromethoxy-substituted phenyl,
is in each case optionally chlorine- or methyl-substituted pyridyl or thienyl,
$R^2$ is preferably in each case optionally fluorine- or chlorine-substituted $C_1$-$C_{10}$-alkyl, $C_2$-$C_{10}$-alkenyl, $C_1$-$C_4$-alkoxy-$C_2$-$C_4$-alkyl,
is optionally methyl- or methoxy-substituted $C_5$-$C_6$-cycloalkyl or
is in each case optionally fluorine-, chlorine-, bromine-, cyano-, nitro-, $C_1$-$C_4$-alkyl-, $C_1$-$C_4$-alkoxy-, trifluoromethyl- or trifluoromethoxy-substituted phenyl or benzyl,
$R^3$ is preferably optionally fluorine-substituted $C_1$-$C_4$-alkyl or is optionally fluorine-, chlorine-, bromine-, $C_1$-$C_4$-alkyl, $C_1$-$C_4$-alkoxy, trifluoromethyl-, trifluoromethoxy-, cyano- or nitro-substituted phenyl,
$R^4$ is preferably in each case optionally fluorine- or chlorine-substituted $C_1$-$C_4$-alkyl, $C_1$-$C_4$-alkoxy, $C_1$-$C_4$-alkylamino, $C_1$-$C_4$-alkylthio or is in each case optionally fluorine-, chlorine-, bromine-, nitro-, cyano-, $C_1$-$C_4$-alkoxy-, trifluoromethoxy-, $C_1$-$C_4$-alkylthio-, —$C_1$-$C_4$-haloalkylthio-, $C_1$-$C_4$-alkyl- or trifluoromethyl-substituted phenyl, phenoxy or phenylthio,
$R^5$ is preferably $C_1$-$C_4$-alkoxy or $C_1$-$C_4$-thioalkyl,
$R^6$ is preferably $C_1$-$C_6$-alkyl, $C_3$-$C_6$-cycloalkyl, $C_1$-$C_6$-alkoxy, $C_3$-$C_6$-alkenyl, $C_1$-$C_4$-alkoxy-$C_1$-$C_4$-alkyl,
$R^7$ is preferably $C_1$-$C_6$-alkyl, $C_3$-$C_6$-alkenyl or $C_1$-$C_4$-alkoxy-$C_1$-$C_4$-alkyl,
$R^6$ and $R^7$ together are preferably an optionally methyl- or ethyl-substituted $C_1$-$C_6$-alkylene radical, in which optionally a carbon atom is replaced by oxygen or sulphur.

V is more preferably oxygen or N-D,
W is more preferably hydrogen, methyl; ethyl, chlorine, bromine or methoxy,
X is more preferably chlorine, bromine, methyl, ethyl, propyl, isopropyl, methoxy, ethoxy or trifluoromethyl,
Y and Z are more preferably independently of one another hydrogen, fluorine, chlorine, bromine, methyl, ethyl, propyl, isopropyl, trifluoromethyl or methoxy,
A is more preferably methyl, ethyl, propyl, isopropyl, butyl, isobutyl, sec-butyl, tert-butyl, cyclopropyl, cyclopentyl or cyclohexyl,
B is more preferably hydrogen, methyl or ethyl,
A, B and the carbon atom to which they are attached are more preferably saturated $C_6$-cycloalkyl, in which optionally a ring member is replaced by oxygen, and which is optionally monosubstituted by methyl, ethyl, trifluoromethyl, methoxy, ethoxy, propoxy or butoxy,
D is more preferably hydrogen, is methyl, ethyl, propyl, isopropyl, butyl, isobutyl, allyl, cyclopropyl, cyclopentyl or cyclohexyl,
A and D are together more preferably optionally methyl-substituted $C_3$-$C_4$-alkanediyl,
G is more preferably hydrogen (a) or is one of the groups

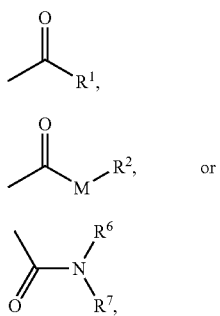

in which
M is oxygen or sulphur,
$R^1$ is more preferably $C_1$-$C_8$-alkyl, $C_2$-$C_4$-alkenyl, methoxymethyl, ethoxymethyl, methylthiomethyl, ethylthiomethyl, cyclopropyl, cyclopentyl or cyclohexyl,
is optionally fluorine-, chlorine-, bromine-, cyano-, nitro-, methyl-, ethyl-, methoxy-, trifluoromethyl- or trifluoromethoxy-substituted phenyl,
is in each case optionally chlorine- or methyl-substituted pyridyl or thienyl,
$R^2$ is more preferably $C_1$-$C_8$-alkyl, $C_2$-$C_4$-alkenyl, methoxyethyl, ethoxyethyl or is phenyl or benzyl,
$R^6$ and $R^7$ are independently of one another more preferably methyl, ethyl or together are a $C_5$-alkylene radical in which the $C_3$-methylene group is replaced by oxygen.
V is very preferably N-D,
W is very preferably hydrogen or methyl,
X is very preferably chlorine, bromine or methyl,
Y and Z are very preferably independently of one another hydrogen, chlorine, bromine or methyl,
A, B and the carbon atom to which they are attached are very preferably saturated $C_6$-cycloalkyl, in which optionally a ring member is replaced by oxygen, and which is optionally monosubstituted by methyl, trifluoromethyl, methoxy, ethoxy, propoxy or butoxy,
D is very preferably hydrogen, G is very preferably hydrogen (a) or is one of the groups

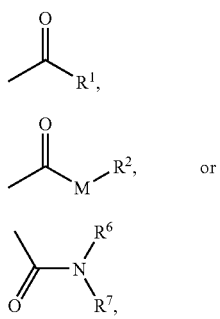

in which
M is oxygen or sulphur,
$R^1$ is very preferably $C_1$-$C_8$-alkyl, $C_2$-$C_4$-alkenyl, methoxymethyl, ethoxymethyl, ethylmethylthio, cyclopropyl, cyclopentyl, cyclohexyl or
is optionally fluorine-, chlorine-, bromine-, methyl-, methoxy-, trifluoromethyl-, trifluoromethoxy-, cyano- or nitro-substituted phenyl,
is in each case optionally chlorine- or methyl-substituted pyridyl or thienyl,
$R^2$ is very preferably $C_1$-$C_8$-alkyl, $C_2$-$C_4$-alkenyl, methoxyethyl, ethoxyethyl, phenyl or benzyl,
$R^6$ and $R^7$ are independently of one another very preferably methyl, ethyl or together are a $C_5$-alkylene radical, in which the $C_3$-methylene group is replaced by oxygen.

Particular preference is given to oil-based oil suspension concentrates comprising compounds of the formula (I")

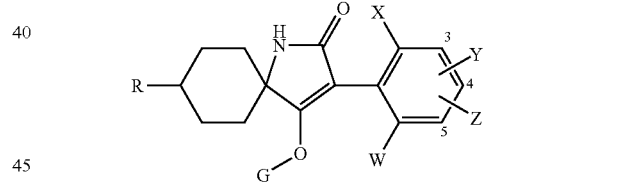

(I")

| Example No. | W | X | Y | Z | R | G | m.p. °C. |
|---|---|---|---|---|---|---|---|
| I"-1 | H | Br | 5-CH₃ | H | OCH₃ | CO-i-C₃H₇ | 122 |
| I"-2 | H | Br | 5-CH₃ | H | OCH₃ | CO₂—C₂H₅ | 140-142 |
| I"-3 | H | CH₃ | 5-CH₃ | H | OCH₃ | H | >220 |
| I"-4 | H | CH₃ | 5-CH₃ | H | OCH₃ | CO₂—C₂H₅ | 128 |
| I"-5 | CH₃ | CH₃ | 3-Br | H | OCH₃ | H | >220 |
| I"-6 | CH₃ | CH₃ | 3-C | H | OCH₃ | H | 219 |
| I"-7 | H | Br | 4-CH₃ | 5-CH₃ | OCH₃ | CO-i-C₃H₇ | 217 |
| I"-8 | H | CH₃ | 4-C | 5-CH₃ | OCH₃ | CO₂C₂H₅ | 162 |
| I"-9 | CH₃ | CH₃ | 3-CH₃ | 4-CH₃ | OCH₃ | H | >220 |
| I"-10 | CH₃ | CH₃ | 3-Br | H | OC₂H₅ | CO-i-C₃H₇ | 212-214 |
| I"-11 | H | CH₃ | 4-CH₃ | 5-CH₃ | OC₂H₅ | CO-n-C₃H₇ | 134 |
| I"-12 | H | CH₃ | 4-CH₃ | 5-CH₃ | OC₂H₅ | CO-i-C₃H₇ | 108 |
| I"-13 | H | CH₃ | 4-CH₃ | 5-CH₃ | OC₂H₅ | CO-c-C₃H₅ | 163 |

Preference is further given to oil-based oil suspension concentrates comprising imidacloprid, thiacloprid, acetamiprid, nitenpyram, clothianidin, thiamethoxam or dinotefuran.

Preference is additionally given to oil-based oil suspension concentrates comprising 1H-pyrazole-5-carboxamide,3- bromo-N-[4-cyano-2-methyl-6-[(methylamino)-carbonyl]phenyl]-1-(3-chloro-2-pyridinyl) (9CI); 1H-pyrazole-5-carboxamide,N-4-cyano-2-methyl-6-[(methylamino)carbonyl]phenyl]-1-(3-chloro-2-pyridinyl)-3-(trifluoromethyl) (9CI); 1H-pyrazole-5-carboxamide,3-bromo-N-[4-chloro-2-methyl-6-[(methylamino)carbonyl]phenyl]-1-(3-chloro-2-pyridinyl) (9CI); 1H-pyrazole-5-carboxamide,N-[4-chloro-2-methyl-6-[[(1-methylethyl)amino]-carbonyl]phenyl]-1-(3-chloro-2-pyridinyl)-3-(trifluoromethyl) (9CI).

Suitable penetrants in the present context are all those substances which are customarily used in order to improve the penetration of active agrochemical substances into plants. Penetrants are defined in this context by their ability to penetrate, from the aqueous spray liquor and/or from the spray covering, into the cuticle of the plant and thereby to increase the mobility of active substances in the cuticle. The method described below and in the literature (Baur et al., 1997, Pesticide Science 51, 131-152) can be used for determining this property.

Preference is given to alkanol alkoxylates of the formula (I)

R—O—(-AO—)$_m$—R'  (I)

in which
R is straight-chain or branched alkyl having 4 to 20 carbon atoms,
R' is methyl, ethyl, n-propyl, isopropyl, n-butyl, isobutyl, t-butyl, n-pentyl or n-hexyl,
AO is an ethylene oxide radical, a propylene oxide radical, a butylene oxide radical or mixtures of ethylene oxide and propylene oxide radicals or mixtures of ethylene oxide and butylene oxide radicals, and
m stands for numbers from 2 to 30:

One particularly preferred group of penetrants are alkanol alkoxylates of the formula (Ia)

R—O—(-EO—)$_n$—R  (Ia)

in which
R and R' have the definitions indicated above,
EO is —CH$_2$—CH$_2$—O— and
n stands for numbers from 2 to 20.

A further particularly preferred group of penetrants are alkanol alkoxylates of the formula (Ib)

R—O—(-EO—)$_p$—(—PO—)$_q$—R'  (Ib)

in which
R and R' have the definitions indicated above,
EO is CH$_2$—CH$_2$—O—,
PO is

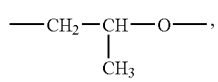

p stands for numbers from 1 to 10 and
q stands for numbers from 1 to 10.

A further particularly preferred group of penetrants are alkanol alkoxylates of the formula (Ic)

R—O—(—PO—)$_r$—(-EO—)$_s$—R'  (Ic)

in which
R and R' have the definitions indicated above,
EO is CH$_2$—CH$_2$—O—,

PO is

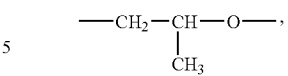

r stands for numbers from 1 to 10 and
s stands for numbers from 1 to 10.

A further particularly preferred group of penetrants are alkanol alkoxylates of the formula (Id)

CH$_3$—(CH$_2$)$_t$—CH$_2$—O—(—CH$_2$—CH$_2$—O—)$_u$— CH$_3$  (Id)

in which
t stands for numbers from 8 to 13
and
u stands for numbers from 6 to 17.

A further particularly preferred group of penetrants are alkanol alkoxylates of the formula (Ie)

R—O—(-EO—)$_p$—(—BO—)$_q$—R'  (Ie)

in which
R and R' have the definitions indicated above,
EO is CH$_2$—CH$_2$—O—,
BO is

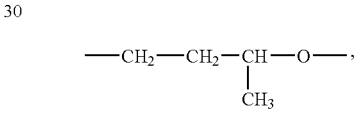

p stands for numbers from 1 to 10 and
q stands for numbers from 1 to 10.

A further particularly preferred group of penetrants are alkanol alkoxylates of the formula (If)

R—O—(—BO—)$_r$—(-EO—)$_s$—R'  (If)

in which
R and R' have the definitions indicated above,
BO is

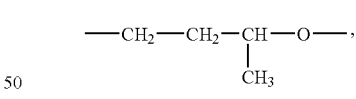

EO is CH$_2$—CH$_2$—O—,
r stands for numbers from 1 to 10 and
S stands for numbers from 1 to 10.

In the formulae indicated above
R is preferably butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

Particularly preferred alkanol alkoxylates of the formula (Ie) include the compound of the formula (Ie-1)

CH$_3$—(CH$_2$)$_{10}$—O—(-EO—)$_6$—(—BO—)$_2$—CH$_3$  (Ie-1)

in which
EO is CH$_2$—CH$_2$—O—,

BO is

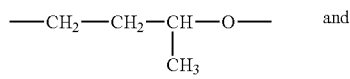 and the numbers 6 and 2 represent average values.

Particular preference is also given to alkanol alkoxylates of the formula (Ie-2)

$$CH_3—(CH_2)_8—O—(-EO—)_8—(—BO—)_2—CH_3 \quad (Ie-2)$$

in which
EO is $CH_2—CH_2—O—$ steht,
BO is

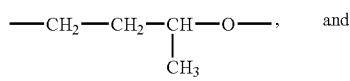, and the numbers 8 and 2 represent average values.

Particularly preferred alkanol alkoxylates of the formula (Id) are compounds of that formula in which
t stands for numbers from 9 to 12 and
u stands for numbers from 7 to 9.

A general definition of the alkanol alkoxylates is given by the above formulae. These substances constitute mixtures of substances of the stated type with different chain lengths. For the indices, therefore, average values are calculated, which may also deviate from whole numbers.

By way of example mention may be made of alkanol alkoxylate of the formula (Id) in which
t stands for the average value 10.5 and
u stands for the average value 8.4.

The "closed" alkanol alkoxylates of the stated formulae are known and available commercially or can be prepared by known methods (EP-A 0 681 865).

By "closed" penetrants are meant, generally, compounds of the formula (I) as described in the application.

By "open" penetrants are meant, generally, compounds of the formula (I) where R' is hydrogen. The penetrants are described in EP-A-681 865.

The compounds of the formula (I') are known:

For 3-acyl-pyrrolidine-2,4-diones pharmaceutical properties have already been described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095).

EP-A-0 262 399 and GB-A-2 266 888 disclose similarly structured compounds (3-aryl-pyrrolidine-2,4-diones). Known compounds include unsubstituted, bicyclic 3-aryl-pyrrolidine-2,4-dione derivatives (EP-A-355 599, EP-A-415 211 and JP-A-12-053 670) and also substituted monocyclic 3-aryl-pyrrolidine-2,4-dione derivatives (EP-A-377 893 and EP-A-442 077).

Also known are polycyclic 3-arylpyrrolidine-2,4-dione derivatives (EP-A-442 073) and also 1H-arylpyrrolidine-dione derivatives (EP-A-456 063, EP-A-521 334, EP-A-596 298, EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/16748, WO 99/24437, WO 99/43649, WO 99/48869 and WO 99/55673, WO 01/17972, WO 01/23354, WO 01/74770, WO 04/024688, WO 04/007448, WO 04/080962 and WO 04/065366).

Additionally $\Delta^3$-dihydrofuran-2-one derivatives are known (cf. DE-A-4 014 420). The synthesis of the tetronic acid derivatives used as starting compounds (such as 3-(2-methylphenyl)-4-hydroxy-5-(4-fluorophenyl)-$\Delta^3$-dihydrofuran-2-one, for example) is likewise described in DE-A-4 014 420. Similarly structured compounds are known from the publication Campbell et al., J. Chem. Soc., Perkin Trans. 1, 1985, (8) 1567-76. Moreover, 3-aryl-$\Delta^3$-dihydrofuranone derivatives are known from EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869, WO 99/55673, WO 01/17 972, WO 01/23354, WO 01/74770, WO 04/024688 and WO 04/080962.

Suitable plant oils include all oils which can normally be used in agrochemical compositions and can be obtained from plants, and mixtures of these oils. Examples that may be mentioned include sunflower oil, rapeseed oil, olive oil, soyabean oil and corn oil.

The oil-based suspension concentrates of the invention comprise at least one nonionic surfactant and/or at least one anionic surfactant.

Suitable nonionic surfactants include all substances of this type that can normally be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and also copolymers of (meth) acrylic acid and (meth)acrylic esters, and also alkyl ethoxylates and alkylaryl ethoxylates, which optionally may be phosphated and optionally may be neutralized with bases, it being possible for mention to be made, by way of example, of sorbitol ethoxylates.

Suitable anionic surfactants include all substances of this type that can normally be used in agrochemical compositions. Preference is given to alkali metal salts and alkaline earth metal salts of alkylsulphonic acids or alkylarylsulphonic acids.

Suitable additives which may be included in the formulations of the invention are emulsifiers, foam inhibitors, preservatives, antioxidants, colorants and inert filler materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxy-propoxylates, it being possible to mention, by way of example, sorbitan derivatives, polyethylene oxide-sorbitan fatty acid esters and sorbitan fatty acid esters.

Suitable foam inhibitors include all substances that can normally be used for this purpose in agrochemical compositions. Preference is given to silicone oils and magnesium stearate.

Suitable preservatives include all substances that can normally be used for this purpose in agrochemical compositions of this type. Examples that may be mentioned include Preventol® (Bayer AG) and Proxel®.

Suitable antioxidants include all substances that can normally be used for this purpose in agrochemical compositions. Preference is given to 2,6-di-tert-butyl-4-methylphenol.

Suitable colorants include all substances that can normally be used for this purpose in agrochemical compositions. By way of example mention may be made of titanium dioxide, pigmentary carbon black, zinc oxide and blue pigments, and also Permanent Red FGR.

Suitable inert filler materials include all substances that can normally be used for this purpose in agrochemical compositions but do not function as thickeners. Preference is given to inorganic particles, such as carbonates, silicates and oxides, and also organic substances, such as urea-formaldehyde condensates. By way of example mention may be made of kaolin, rutile, silicon dioxide, so-called highly disperse silica, silica gels, and also natural and synthetic silicates, and additionally talc.

The amount of the individual components can be varied within a relatively wide range in the oil-based suspension concentrates of the invention. Thus the concentrations

- of active agrochemical substance are generally between 5% and 30%, preferably between 10% and 25% by weight,
- of "closed" penetrant are generally between 5% and 30%, preferably between 15% and 25% by weight,
- of vegetable oil or mineral oil are generally between 20% and 55%, preferably between 25% and 50% by weight,
- of surfactants are generally between 2.5% and 30%, preferably between 5.0% and 25% by weight, and
- of additives are generally between 0% and 25%, preferably between 0% and 20% by weight.

The oil-based suspension concentrates of the invention are produced by mixing the components with one another in the respectively desired proportions. The order in which the constituents are combined with one another is arbitrary. Appropriately the solid components are used in a finely ground state. It is, however, also possible to subject the suspension which results after the constituents have been combined first to a coarse grinding and then to a fine grinding, so that the mean particle size is below 20 μm. Preferred suspension concentrates are those in which the solid particles have a mean size between 1 and 10 μm.

The temperatures when carrying out the process of the invention can be varied within a certain range. The work is carried out generally at temperatures between 10° C. and 60° C., preferably between 15° C. and 40° C. Equipment suitable for carrying out the process of the invention includes customary mixing and grinding apparatus which is used for producing agrochemical formulations.

The oil-based suspension concentrates of the invention constitute formulations which remain stable even following prolonged storage at elevated temperatures or in the cold, since no crystal growth is observed. By dilution with water they can be converted into homogeneous spray liquids. These spray liquids are applied by customary methods, i.e., for example, by spraying, pouring or injecting.

The application rate of the oil-based suspension concentrates of the invention can be varied within a relatively wide range. It is guided by the particular active agrochemical substances and by their amount in the formulations.

With the aid of the oil-based suspension concentrates of the invention it is possible to deliver active agrochemical substances to plants and/or their habitat in a particularly advantageous way. The active agrochemical substances included develop a better biological activity (in particular a better agrochemical activity and/or better crop tolerance) than in the case of application in the form of the corresponding conventional formulations.

In accordance with the invention it is possible to treat all plants and plant parts. By plants here are meant all plants and plant populations, such as desirable and unwanted wild plants or crop plants (including naturally occurring crop plants). Crop plants may be plants which can be obtained by conventional breeding and optimization methods or by biotechnological and gene-technological methods or combinations of these methods, including the transgenic plants and including the plant cultivars which can or cannot be protected by varietal property rights. By plant parts are to be meant all above-ground and below-ground parts and organs of the plants, such as shoot, leaf, flower and root, an exemplary listing embracing leaves, needles, stems, trunks, flowers, fruit bodies, fruits and seeds and also roots, tubers and rhizomes. The plant parts also include harvested material and also vegetative and generative propagation material, examples being seedlings, tubers, rhizomes, cuttings and seeds.

The treatment of the plants and plant parts in accordance with the invention with the suspension concentrates is carried out directly or by action on their environment, habitat or storage area in accordance with the customary treatment methods, for example by dipping, spraying, squirting, evaporating, atomizing, or brush application and, in the case of propagation material, especially seeds, additionally by single or multiple coating.

As already mentioned above, all plants and their parts can be treated in accordance with the invention. In one preferred embodiment, wild plant species and plant varieties, or those obtained by conventional biological breeding methods, such as crossing or protoplast fusion, and also parts thereof, are treated. In a further preferred embodiment transgenic plants and plant varieties, which have been obtained by gene-technological methods in combination where appropriate with conventional methods (genetic modified organisms), and parts thereof, are treated. The term "parts" or "parts of plants" or "plant parts" has been elucidated above.

With particular preference, plants of the plant varieties that are in each case available commercially or in use are treated in accordance with the invention. By plant varieties are meant plants having novel properties (traits) which have been bred by conventional breeding, by mutagenesis or by recombinant DNA techniques. They may be varieties, biotypes and genotypes.

Depending on the plant species or plant varieties, their location and growth conditions (soils, climate, vegetation period, nutrition) the treatment according to the invention may also result in superadditive (synergistic) effects. Thus, for example, reduced application rates and/or extensions in the spectrum of action and/or an increase in the effect of the substances and compositions that can be used in accordance with the invention, better plant growth, increased tolerance to high or low temperatures, increased tolerance to drought or to water content or soil salt content, increased flowering performance, easier harvesting, accelerated maturation, higher harvesting yields, greater quality and/or higher nutritional value of the harvested products, higher storage capacity and/or processing capability of the harvested products are possible that go beyond the effects that were actually to be expected.

The preferred transgenic (i.e., obtained by gene technology) plants or plant varieties for treatment in accordance with the invention include all plants which by virtue of the gene-technological modification received genetic material which endows these plants with particularly advantageous, valuable traits. Examples of such traits are better plant growth, increased tolerance to high or low temperatures, increased tolerance to drought or to water content or soil salt content, increased flowering performance, easier harvesting, accelerated maturation, higher harvesting yields, greater quality and/or higher nutritional value of the harvested products, higher storage capacity and/or processing capability of the harvested products. Further and particularly emphasized examples of such traits are a heightened defence of the plants against animal and microbial pests, such as against insects, mites, phytopathogenic fungi, bacteria and/or viruses, and also increased tolerance of the plants to particular active herbicidal substances. Examples of transgenic plants include the important crop plants, such as cereals (wheat, rice), maize, soya, potatoes, cotton, oilseed rape, beet, sugar cane and also fruit plants (with the fruits apples, pears, citrus fruits and grapes), particular emphasis being given to maize, soya, potatoes, cotton and oilseed rape. Traits given particular emphasis are the heightened defence of the plants against insects, by means of toxins which form in the plants, particularly those generated in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) ("Bt plants" below). Further traits given particular emphasis are the increased defence of plants against fungi, bacteria and viruses as a result of Systemic Acquired Resistance (SAR), systemin, phytoalexins, elicitors and also resistance genes, and proteins and toxins expressed accordingly. Further traits given particular emphasis include the increased tolerance of the plants to certain active herbicidal substances, examples being imidazolinones, sulphonylureas, glyphosate or phosphinotricin (e.g. "PAT" gene). The genes which impart the desired traits in each case may also occur in combinations with one another in the transgenic plants. Examples that may be mentioned of "Bt plants" include maize varieties, cotton varieties, soya varieties and potato varieties which are sold under the trade names YIELD GARD® (e.g. maize, cotton, soya), KnockOut® (e.g. maize), StarLink® (e.g. maize), Bollgard® (cotton), Nucotn® (cotton) and NewLeaf® (potato). Examples that may be mentioned of herbicide-tolerant plants include maize varieties, cotton varieties and soya varieties which are sold under the trade names Roundup Ready® (tolerance to glyphosate, e.g. maize, cotton, soya), Liberty Link® (tolerance to phosphinotricin, e.g. oilseed rape), IMI® (tolerance to imidazolinones) and STS® (tolerance to sulphonylureas, e.g. maize). Herbicide-resistant plants (bred conventionally for herbicide tolerance) that may be mentioned also include the varieties (e.g. maize) sold under the name Clearfield®. It will be appreciated that these remarks also apply to plant varieties to be developed in the future or to appear on the market in the future and possessing these genetic traits or genetic traits developed in the future.

The plants recited can be treated with particular advantage with the suspension concentrates of the invention. The ranges of preference indicated above for the suspension concentrates also apply to the treatment of these plants. Particular emphasis may be given to the treatment of plants with the suspension concentrates recited specifically in the present text.

The invention is illustrated by the following examples.

PREPARATION EXAMPLES

Example 1

To prepare a suspension concentrate

| | |
|---|---|
| 100.0 g | of the compound of Example (I''-4) |
| 100.0 g | of polyoxyethylene-sorbitol oleate |
| 90.0 g | of a mixture of polyalkoxylated alcohols (Atlox 4894) |
| 10.0 g | of lignin sulphonate (Borresperse NA) |
| 0.5 g | of polydimethylsiloxane |
| 2.0 g | of 2,6-di-tert-butyl-n-methylphenol |
| 2.0 g | of anhydrous citric acid | are introduced with stirring at room temperature into a mixture of

| | |
|---|---|
| 250.0 g | of the compound of the formula (Ie-2) and |
| 440.0 g | of sunflower oil. |

After the end of addition the mixture is stirred at room temperature for a further 10 minutes. The resultant homogeneous suspension is subjected first to coarse grinding and then to fine grinding, giving a suspension in which 90% of the particulate solids have a particle size below 6 µm.

Example 2

To prepare a suspension concentrate

| | |
|---|---|
| 100.0 g | of the compound of Example (I''-4) |
| 100.0 g | of polyoxyethylene-sorbitol oleate |
| 100.0 g | of a mixture of polyoxyethylene fatty acid glyceride (Atlas G 1281) |
| 0.5 g | of polydimethylsiloxane |
| 2.0 g | of 2,6-di-tert-butyl-n-methylphenol |
| 2.0 g | of anhydrous citric acid | are introduced with stirring at room temperature into a mixture of

| | |
|---|---|
| 250.0 g | of the compound of the formula (Ie-1) and |
| 445.0 g | of sunflower oil. |

After the end of addition the mixture is stirred at room temperature for a further 10 minutes. The resultant homogeneous suspension is subjected first to coarse grinding and then to fine grinding, giving a suspension in which 90% of the particulate solids have a particle size below 6 µm.

Example 3

To prepare a suspension concentrate

| | |
|---|---|
| 200.0 g | of imidacloprid |
| 100.0 g | of polyoxyethylene-sorbitol oleate |
| 70.0 g | of a mixture of polyalkoxylated alcohols (Atlox 4894) |
| 30.0 g | of lignin sulphonate (Borresperse NA) |
| 0.5 g | of polydimethylsiloxane |
| 2.0 g | of 2,6-di-tert-butyl-n-methylphenol |
| 2.0 g | of anhydrous citric acid | are introduced with stirring at room temperature into a mixture of

| | |
|---|---|
| 200.0 g | of the compound of the formula (Ie-2) and |
| 400.0 g | of sunflower oil. |

After the end of addition the mixture is stirred at room temperature for a further 10 minutes. The resultant homogeneous suspension is subjected first to coarse grinding and then to fine grinding, giving a suspension in which 90% of the particulate solids have a particle size below 6 µm.

Comparative Example I

To prepare a suspension concentrate

| | |
|---|---|
| 100.0 g | of the compound of Example (I'-4) |
| 100.0 g | of polyoxyethylene-sorbitol oleate |
| 90.0 g | of a mixture of polyalkoxylated alcohols (Atlox 4894) |
| 10.0 g | of lignin sulphonate (Borresperse NA) |
| 0.5 g | of polydimethylsiloxane |
| 2.0 g | of 2,6-di-tert-butyl-4-methylphenol |
| 2.0 g | of anhydrous citric acid | are introduced with stirring at room temperature into a mixture of

| | |
|---|---|
| 250.0 g | of the compound of the formula<br>$CH_3-(CH_2)_8-O-(EO)_8-(BO)_2-H$<br>in which<br>EO is $CH_2-CH_2-O-$,<br>BO is $-CH_2-CH_2-CH(CH_3)-O-$ and<br>the numbers 8 and 2 represent average values, and |
| 440.0 g | of sunflower oil. |

After the end of addition the mixture is stirred at room temperature for a further 10 minutes. The resultant homogeneous suspension is subjected first to coarse grinding and then to fine grinding, giving a suspension in which 90% of the particulate solids have a particle size below 6 μm.

Comparative Example 2

To prepare a suspension concentrate

| | |
|---|---|
| 200.0 g | of imidacloprid |
| 100.0 g | of polyoxyethylene-sorbitol oleate |
| 70.0 g | of a mixture of polyalkoxylated alcohols (Atlox 4894) |
| 30.0 g | of lignin sulphonate (Borresperse NA) |
| 0.5 g | of polydimethylsiloxane |
| 2.0 g | of butylhydroxytoluene |
| 2.0 g | of anhydrous citric acid | are introduced with stirring at room temperature into a mixture of

| | |
|---|---|
| 200.0 g | of the compound of the formula<br>$CH_3-(CH_2)_8-O-(EO)_8-(BO)_2-H$<br>in which<br>EO is $CH_2-CH_2-O-$,<br>BO is $-CH_2-CH_2-CH(CH_3)-O-$ and<br>the numbers 8 and 2 represent average values, and |
| 400.0 g | of sunflower oil. |

After the end of addition the mixture is stirred at room temperature for a further 10 minutes. The resultant homogeneous suspension is subjected first to coarse grinding and then to fine grinding, giving a suspension in which 90% of the particulate solids have a particle size below 6 μm.

APPLICATION EXAMPLES

Example I

Test Description: Penetrants at the Level of the Cuticle

Additives which act as penetrants at the level of the cuticle may be referred to below as accelerator additives (cf. Schönherr and Baur, 1994, Pesticide Science 42, 185-208). The feature of accelerator additives is their ability to penetrate from the aqueous spray liquor and/or from the spray covering into the cuticle and thereby to increase the mobility of active substances in the cuticle. Other additives such as polyethylene glycol, in contrast, act only in the spray covering (via the liquid phase) or act only as wetting agents, such as sodium dodecyl sulphate, for example.

This test determines the influence of additives on the penetration properties of other substances at the level of the cuticle. The mobility of the test substance in the cuticle is measured with and without an additive, by way of a desorption method. The method is published in detail in the literature (Baur et al., 1997, Pesticide Science, 51, 131-152) and only the principles and any deviations are described below.

As a test substance with the function of a tracer a selection was made here of a radiolabelled weak organic acid. Plant material used comprised the enzymatically isolated leaf cuticles of the top face of peach leaves from outdoor trees. The cuticles were installed in specially manufactured stainless steel diffusion cells. The tracer, in a citrate buffer at a pH of 3 in the dissolved state, was applied to the side originally facing the inside of the leaf. This inner side readily takes up the small radioactive amount of the tracer in the undissociated acid form. Subsequently this inner side was covered and maintained at 100% atmospheric humidity. The morphological outer side of the leaf cuticle, normally exposed to the air, was then contacted with a buffer (pH 7), with the receptor solution, and the desorption was started. The penetrated acid form of the test substance is dissociated by the receptor and the desorption follows first-order kinetics. The desorption constant is proportional to the mobility of the tracer in the cuticle.

After at least 2 times for determining this constant, the desorption is then continued with a buffer which additionally includes the test additive. Depending on the property of the additive there is then sorption of the additive in the cuticle and, depending on its activity as a plasticizer for the cuticle, there is an increase in the mobility of the tracer within the cuticle. This is manifested in an increased desorption constant, and the ratio of the slopes with additive to that without additive describes the effect of the additive to act as a penetrant at the level of the cuticle. The comparison of the average effect of different additives shows their effectiveness at acting as cuticle plasticizers.

Result:

Effect of closed (methylated) and open (non-methylated) additives on the mobility of active substance (here, a weak organic acid) in the cuticle. Additives used were a methylated or non-methylated isotridecyl-(6) ethoxylate and the above-mentioned penetrants Ie-1 and Ie-2 and also their open forms Ie'-1 and Ie'-2.

| Additive | Average effect | SE (standard error) |
| --- | --- | --- |
| Isotridecyl-(6) ethoxylate, open | 42.3 | 9.3 |
| Isotridecyl-(6) ethoxylate, closed | 78.9 | 21.5 |
| Ie'-1, open | 9.0 | 1.8 |
| Ie-1 (=closed) | 78.4 | 26.1 (additive from Example 2) |
| Ie'-2, open | 45.1 | 14.3 |
| Ie-2, (=closed) | 89.1 | 19.1 (additive from Example 1) |

Example II

Penetration Test

This test measures the penetration of active substances through enzymatically isolated cuticles of apple leaves.

The leaves used are cut in the fully developed state from apple trees of the Golden Delicious variety. The cuticles are isolated as follows:

- first of all, leaf discs labelled on the underside with dye and formed by punching were filled by means of vacuum infiltration with a pectinase solution (0.2% to 2% strength) buffered to a pH of between 3 and 4,
- then sodium azide was added and
- the leaf discs thus treated were left to stand until the original leaf structure broke down and the non-cellular cuticle underwent detachment.

Thereafter only those cuticles from the top leaf sides that were free from stomata and hairs were used. They were washed a number of times in alternation with water and with a buffer solution, pH 7. The clean cuticles obtained were, finally, applied to Teflon plaques, smoothed with a gentle jet of air, and dried.

In the next step the cuticular membranes obtained in this way were place in stainless steel diffusion cells (=transport chambers) for the purpose of membrane transport investigations. For these investigations the cuticles were placed centrally using tweezers on the edges of the diffusion cells, which were coated with silicone grease, and sealed with a ring, which was likewise greased. The arrangement is chosen so that the morphological outer face of the cuticles is directed outwards, in other words to the air, while the original inner side is facing the interior of the diffusion cell. The diffusion cells are filled with water or with a mixture of water and solvent.

Penetration is determined by applying 10 µl of a spray liquor, containing 0.1 g/l active substance, of the formulations indicated below, to the outer face of each cuticle Mains water is used in each of the spray liquors.

After the spray liquors have been applied the water is evaporated in each case and then the chambers are inverted and placed in thermostated troughs, with air of a defined humidity and temperature being blown onto the outer face of the cuticle in each case. The penetration which begins therefore takes place at a relative atmospheric humidity of 60% and a set temperature of 20° C. At regular intervals, samples are taken using a syringe and the amount of penetrated active substance is measured.

The results of the experiment are apparent from the tables. The figures shown are averages of 5 measurements.

TABLE Ia

Penetration of the compound of Example (I''-4) from OD formulations through apple leaf cuticles

| | Penetration (in %) | |
| --- | --- | --- |
| Formulation | after 10 hours | after 23 hours |
| Example 1 | 19 | 34 |
| Comparative example 1 | 12 | 19 |

TABLE Ib

Penetration of imidacloprid from OD formulations through apple leaf cuticles

| | Penetration (in %) | | |
| --- | --- | --- | --- |
| Formulation | after 3 hours | after 12 hours | after 24 hours |
| Example 3 | 22 | 48 | 61 |
| Comparative example 2 | 11 | 35 | 50 |

Example III

Penetration Test (see Ex. II)

| Spray liquor A | |
| --- | --- |
| 0.1 g | of the compound of Ex. (I''-4) |
| 0.25 g | of a compound of the formula (Ie-2) |
| 0.44 g | of sunflower oil |
| 0.1 g | of polyoxyethylene-sorbitol oleate |
| 0.07 g | of a mixture of polyalkoxylated alcohols (Atlox 4894) |
| 0.03 g | of lignin sulphonate (Borresperse NA) in 1 litre of water |

| Spray liquor B | |
| --- | --- |
| 0.1 g | of the compound of Ex. (I''-4) |
| 0.4 g | of a compound of the formula (Ie-2) |
| 0.1 g | of polyoxyethylene-sorbitol oleate |
| 0.07 g | of a mixture of polyalkoxylated alcohols (Atlox 4894) |
| 0.03 g | of lignin sulphonate (Borresperse NA) in 1 litre of water |

| Spray liquor C | |
| --- | --- |
| 0.1 g | of the compound of Ex. (I''-4) |
| 0.7 g | of sunflower oil |
| 0.1 g | of polyoxyethylene-sorbitol oleate |
| 0.07 g | of a mixture of polyalkoxylated alcohols (Atlox 4894) |
| 0.03 g | of lignin sulphonate (Borresperse NA) in 1 litre of water |

| Spray liquor D | |
|---|---|
| 0.1 g | of the compound of Ex. (I''-4) |
| 0.02 g | of tristearylphenol-(29) ethoxylate |
| 0.1 g | of glycerol |
| | in 1 litre of water |

TABLE II

| | Active substance penetration in % after | | |
|---|---|---|---|
| | 1.5 h | 10 h | 22 h |
| A | 11 | 31 | 47 |
| B | 5 | 22 | 33 |
| C | 2 | 7 | 16 |
| D | | | <5 |

The invention claimed is:

1. An oil-based suspension concentrate, comprising
at least one room-temperature-solid active agrochemical substance selected from the group consisting of spirotetramat and imidacloprid
at least one closed penetrant,
at least one vegetable oil or mineral oil,
at least one nonionic surfactant,
at least one anionic surfactant, and
optionally one or more additives selected from the group consisting of emulsifiers, foam inhibitors, preservatives, antioxidants, colorants, inert filler materials, and combinations thereof, wherein said penetrant is a compound of formula (Ie-1)

$$CH_3—(CH_2)_{10}—O—(-EO—)_6—(—BO—)_2—CH_3 \qquad (Ie-1)$$

in which
EO is $CH_2—CH_2—O—$,
BO is

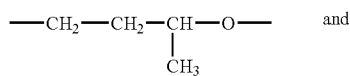   and the numbers 6 and 2 represent average values, or a compound of formula (Ie-2)

$$CH_3—(CH_2)_8—O—(-EO—)_8—(—BO—)_2—CH_3 \qquad (Ie-2)$$

in which
EO is $CH_2—CH_2—O—$,
BO is

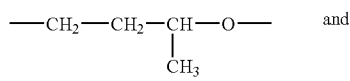   and the numbers 8 and 2 represent average values.

2. The suspension concentrate according to claim 1, wherein said penetrant is a compound of formula (Ie-1)

$$CH_3—(CH_2)_{10}—O—(-EO—)_6—(—BO—)_2—CH_3 \qquad (Ie-1)$$

in which
EO is $CH_2—CH_2—O—$,
BO is

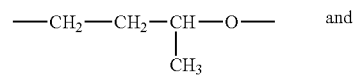   and the numbers 6 and 2 represent average values.

3. The suspension concentrate according to claim 1, wherein said penetrant is a compound of formula (Ie-2)

$$CH_3—(CH_2)_8—O—(-EO—)_8—(—BO—)_2—CH_3 \qquad (Ie-2)$$

in which
EO is $CH_2—CH_2—O—$,
BO is

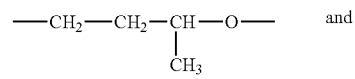   and the numbers 8 and 2 represent average values.

4. The suspension concentrate according to claim 1, wherein said vegetable oil is sunflower oil, rapeseed oil, olive oil, corn oil, soya-bean oil, or a combination thereof.

5. The suspension concentrate according to claim 1, wherein
said active agrochemical substances is between 5% and 30% by weight,
said closed penetrant is between 5% and 30% by weight,
said vegetable oil or mineral oil is between 20% and 55% by weight,
said surfactants is between 2.5% and 30% by weight, and
said additives is between 0% and 25% by weight.

6. The oil-based suspension concentrate according to claim 1, wherein said room-temperature-solid active agrochemical substance is spirotetramat.

7. The oil-based suspension concentrate according to claim 1, wherein said room-temperature-solid active agrochemical substance is imidacloprid.

8. A process for producing suspension concentrates according to claim 1, comprising mixing
at least one of said room-temperature-solid active agrochemical substance,
at least one of said closed penetrant,
at least one vegetable oil or mineral oil,
at least one nonionic surfactant, or at least one anionic surfactant, or a combination thereof, and
optionally one or more additives selected from the group consisting of emulsifiers, foam inhibitors, preservatives, antioxidants, colorants, inert filler materials, and a combination thereof, and
optionally grounding the resulting suspension.

9. A process comprising, applying one or more suspension concentrates according to claim 1 to plants, their habitat, or a combination thereof.

10. A composition comprising, a suspension concentrate according to claim 1 and one or more extenders, one or more surface-active reagents, or a combination thereof.

11. A process for controlling insects, comprising contacting one or more suspension concentrates according to claim 1 with said insects, their habitat, or a combination thereof.

* * * * *